United States Patent [19]

Wei et al.

[11] Patent Number: 5,718,252

[45] Date of Patent: Feb. 17, 1998

[54] DENTAL FLOSS HOLDER

[76] Inventors: Kuang-Hsing Wei; Kuang-Hung Wei, both of 18500 Bay Leaf Way, Germantown, Md. 20874

[21] Appl. No.: 584,119

[22] Filed: Jan. 11, 1996

Related U.S. Application Data

[63] Continuation-in-part of Ser. No. 528,889, Sep. 15, 1995, Pat. No. 5,570,710.

[51] Int. Cl.⁶ .............................. A45D 2/00; A45D 2/38; A45D 2/46

[52] U.S. Cl. .................. 132/323; 132/326; 132/327; 132/329

[58] Field of Search ............................ 132/321, 323, 132/324, 326, 327, 328, 329

[56] References Cited

U.S. PATENT DOCUMENTS

| | | | |
|---|---|---|---|
| 2,644,469 | 7/1953 | Cohen | 132/324 |
| 4,050,470 | 9/1977 | Miller | 132/323 |
| 4,403,625 | 9/1983 | Sanders et al. | 132/323 |
| 5,199,452 | 4/1993 | Cheng | 132/323 |
| 5,503,168 | 4/1996 | Wang | 132/323 |

*Primary Examiner*—Gene Mancene
*Assistant Examiner*—Pedro Philogene

[57] ABSTRACT

A pair of reusable dental floss holders are for securely fastening a length of dental floss at its ends in lieu of winding ends of the dental floss around fingers. Each holder comprises a retaining member having a notch and a slot. The dental floss is inserted into the slot, winding around the retaining member, and then inserted into the slot again to securely fasten the dental floss.

28 Claims, 2 Drawing Sheets

DENTAL FLOSS HOLDER

This application is a CIP of application Ser. No. 08/528,889 filed Sep. 15, 1995, now U.S. Pat. No. 5,570,710.

BACKGROUND OF THE INVENTION

1. The Field of the Invention

This invention relates to the teeth cleaning with a length of dental floss and provides as its general object an improved device which is used to securely fasten dental floss and to render teeth-cleaning more effectively.

2. Description of the Prior Art

There are many devices attempting to render flossing less tedious and make it more effective and convenient. Moreover, a growing number of dentists and orthodontists recommend highly for cleaning teeth daily by using dental floss to remove good particles between teeth. However, most people still don't floss daily, even those who take teeth-cleaning and dental care seriously. The inconvenience and discomfort for maneuvering the dental floss by winding ends of a length of dental floss around two fingers is the main reason. The winding ends of a length of dental floss around two fingers will not only cause discomfort on fingers but also render difficulties in manipulating in mouth. Although there are numerous devices with a predetermined length of floss fixed in two-pronged dental devices, maneuvering with two fingers winding a length of dental floss is still the most effective way of daily dental floss cleaning, especially for reaching and positioning between the rear most teeth, and is highly recommended by the dental profession. U.S. Pat. No. 4,050,470 to Miller (1977) provides a dental floss holder with an inwardly tapered slot extending along one elongate edge which does not securely fasten the dental floss securely in place to facilitate the manipulating of the floss in mouth. Also, the floss tends to be pulled out of the slot during flossing operation which requires different angles for inserting floss in between teeth at different positions.

SUMMARY OF THE INVENTION

It is a general object of the invention to provide a dental floss holder and a method for fastening one end of a dental floss. A pair of reusable dental floss holders are provided for securely fastening the dental floss at its ends in lieu of winding ends of the dental floss around fingers. Each holder comprises a retaining member having a notch and a slot. The dental floss is inserted into the slot, winding around the retaining member, and then inserted into the slot again to securely fasten the dental floss.

Accordingly, several objects and advantages of the present invention are:

(a) to provide an improved dental floss holder which is used to eliminate the discomfort caused by winding a length of dental floss around fingers;

(b) to provide an improved dental floss holder which is designed to save the wasteful of floss for winding an extra length of dental floss around fingers;

(c) to provide an improved dental floss holder to securely fasten dental floss ends than wind around fingers which is needed to be rewound several times during the course of teeth-cleaning; and (d) to provide an improved dental floss holder to better control of a strained dental floss and perform a more effective teeth-cleaning.

Further objects and advantages of the invention will become apparent from the appended drawings and the ensuing specifications.

DRAWING FIGURES

Figure 3:
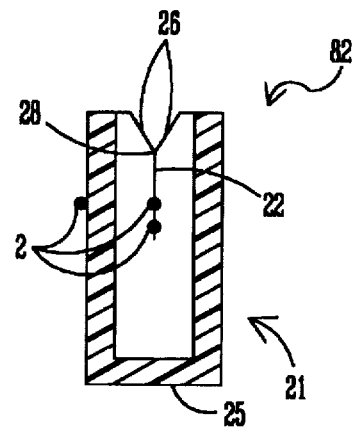
FIG. 3 is a sectional elevation of the dental floss holder in position taken on the line 3—3 of FIG. 2.
Figure 6:
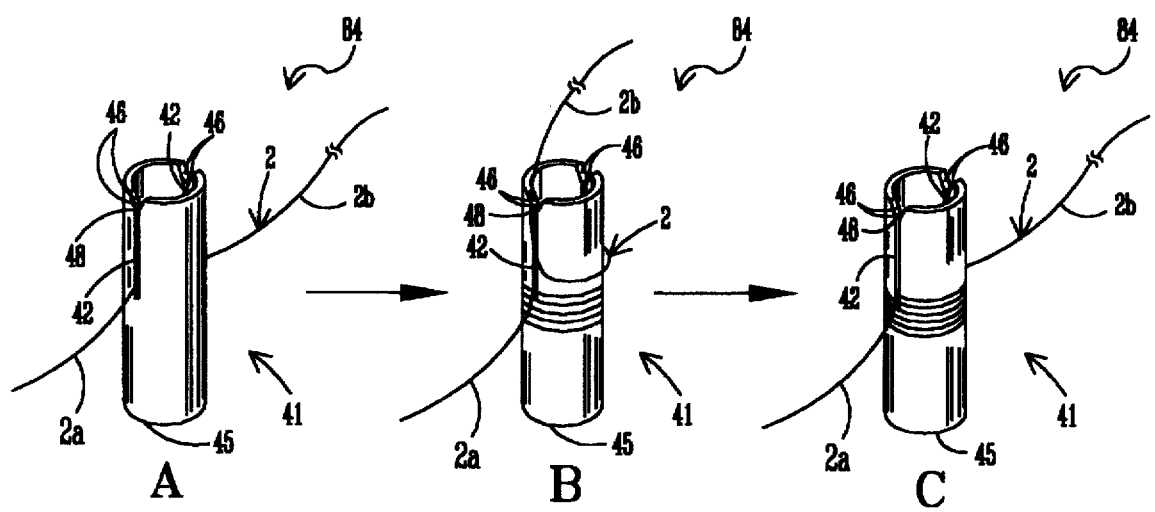
Figure 7:
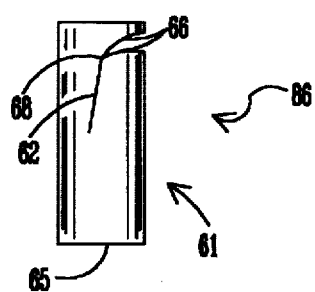

FIGS. 4A–E is an illustration of a notch at different angles with a slot in FIG. 3;

FIGS. 5A–C is an illustration of the method of fastening one end of the dental floss;

FIGS. 6A–C is still an illustration of the method of fastening one end of the dental floss; and FIG. 7 is a perspective view of an alternative embodiment of the dental floss holder.

DETAILED DESCRIPTION OF THE PREFERRED EMBODIMENT

Figure 1:
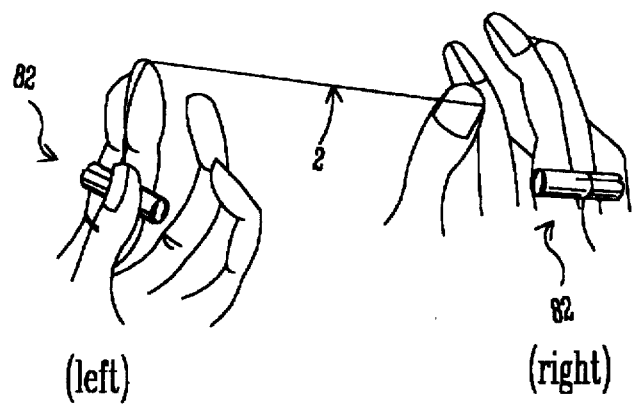
FIG. 1 is a perspective view showing the use of dental floss holders with a dental floss fastened on each holder.
Figure 2:
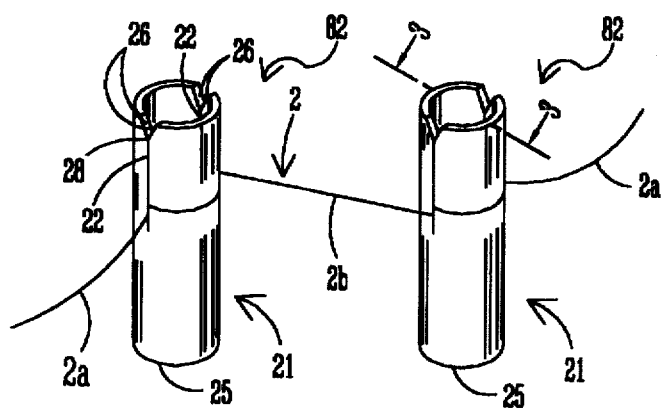
FIG. 2 is a perspective view of the dental floss holders, shown in FIG. 1, connecting in pairs with the dental floss.

FIGS. 1 and 2 illustrate a length of conventional dental floss 2 connecting two identical dental floss holders 82. Dental floss 2 includes a section 2b and two sections 2a. Each section 2a defines each end portion of dental floss 2 extending out from dental floss holder 82. Section 2b defines the portion of dental floss 2 between dental floss holders 82 and connects both holders 82. Each dental floss holder 82 is easily manipulated by each hand so that dental floss 2 is ready to be used inside mouth to clean teeth (not shown) as one usually does with both ends of a dental floss winding around fingers. One of dental floss holders 82 may be held by one hand (left in FIG. 1) and the other holder may be supported by the back of the other hand (right in FIG. 1) to clean teeth. Dental floss holders 82 provide much better control of dental floss 2 and eliminate the discomfort by winding ends of a dental floss around fingers. A single holder may be used on one hand with the opposite end of the dental floss fastened by some other means or by fingers; however, it is expected that two holders will be used. Dental floss holder 82 is suitable for use with the conventional thread or cord type of dental floss or with ribbon or band type of floss. It should be understood that the term "dental floss" is used generically to indicate any type of floss.

Referring now to FIGS. 2 and 3, each dental floss holder 82 comprises a retaining member 21 for retaining each end of dental floss 2. Retaining member 21 preferably comprises a substantially elongated cylindrical piece of material dimensioned to be easily handled by fingers when retaining dental floss 2 and cleaning teeth. Retaining member 21 has a bottom 25 defining the bottom end of retaining member 21.

Referring again to FIGS. 2 and 3, each dental floss holder 82 also comprises receiving means for receiving each end of dental floss 2 to facilitate the retention of dental floss 2. In the preferred form of the invention the receiving means comprises a notch 26 defining an angular cut opening through substantially the opposite end of bottom 25.

Referring still to FIGS. 2 and 3, each dental floss holder 82 also comprises fastening means for fastening each end of dental floss 2. In the preferred form of the invention the fastening means comprises a slit, gap, or slot 22 which is a strip of a narrow cut comprising two substantially parallel lines adjacent to each other closely. The preferred perpendicular distance between the two parallel lines is substantially equal to zero so as to effectively securely fasten dental floss 2 therebetween. However, when the perpendicular distance is substantially equal to or slightly larger than the cross-sectional dimension of dental floss 2, the configuration is still workable in the present invention which will be discussed later in details. The narrow cut of slot 22 is integrally formed substantially on the opposite end of bottom 25. Slot 22 extends or cuts into retaining member 21 substantially toward bottom 25 to an intermediate position in retaining member 21. Preferably, the longitudinal length of slot 22 is substantially equal to one-half the longitudinal length of retaining member 21. Accordingly, slot 22 divides or cuts retaining member 21 into two substantially semicircular pieces of material about half way through to substantially the middle of retaining member 21. Slot 22 connects with notch 26 preferably at a connection line 28 defining a line where the angular cut of notch 26 converges or meets together so that the only action required to insert dental floss 2 from notch 26 into slot 22 is a downward force to pull dental floss 2 into slot 22.

Figure 4:
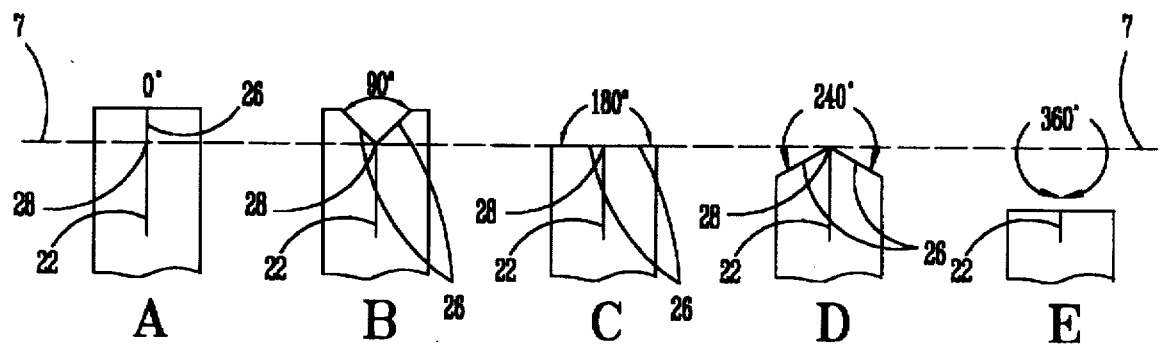

Referring now to FIGS. 3 and 4 from A to E, notch 26 is preferably integrally formed substantially on the opposite end of bottom 25. Notch 26 comprises an angular cut through substantially the opposite end of bottom 25. Slot 22 connects with notch 26 at connection line 28 remote from the opening cut of notch 26. Slot 22 extends substantially longitudinally from connection line 28 deeper toward bottom 25 in retaining member 21. Slot 22 comprises two substantially parallel lines adjacent to each other closely. Notch 26 may start from the angle of zero degree and increase to 360°, as shown in FIG. 4 from A to E. A dashed line 7 is presented to show the relative positions of connection line 28 at different degrees of the angular cut. However, the preferred angles are between 40° and 120° in the present invention. For example, when the degree is zero (A of FIG. 4), notch 26 functions substantially the same as slot 22 does in the case where the perpendicular distance is substantially equal to zero, which will tightly receive dental floss 2 into notch 26 and slot 22. When the degree is 180° (C of FIG. 4), notch 26 becomes flat. When the degree is 240° (D of FIG. 4), notch 26 turns downward. The longitudinal depth of notch 26 into retaining member 21 from the opening of notch 26 to connection line 28 is substantially equal to one-tenth the longitudinal length of retaining member 21. The longitudinal length of slot 22 starting from connection line 28 toward bottom 25 is substantially equal to one-half the longitudinal length of retaining member 21 in this form of the invention. Therefore, when the degree of notch 26 is 360° (E of FIG. 4), notch 26 disappears and cuts out the top portion of slot 22 of retaining member 21. The longitudinal length of slot 22 becomes four-tenths that of retaining member 21 (subtract notch 26, one-tenth the longitudinal length of retaining member 21, from slot 22, one-half the longitudinal length of retaining member 21). Slot 22 having four-tenths the longitudinal length of retaining member 21 can still effectively fasten dental floss 2.

Figure 5:
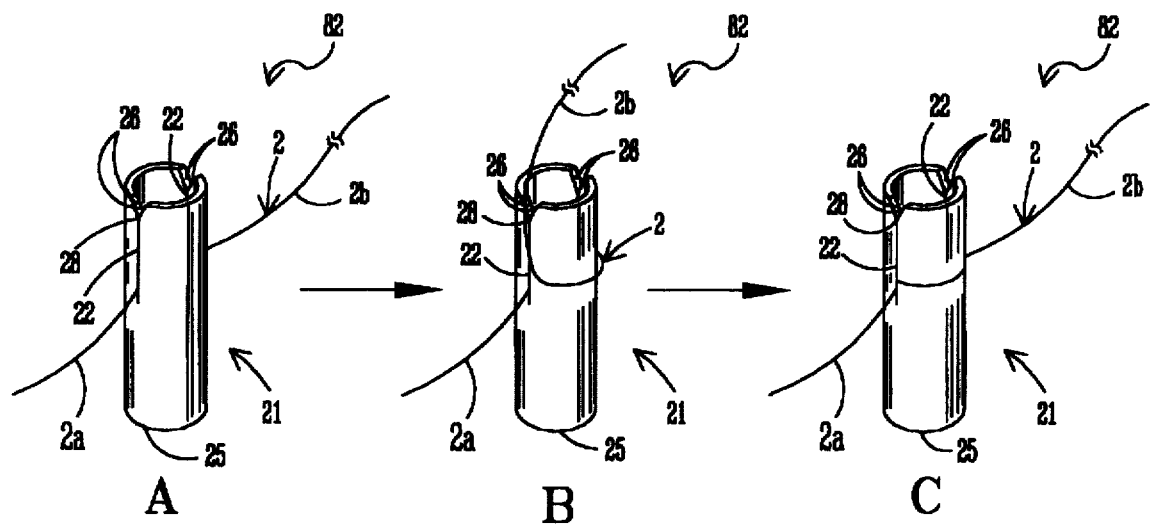

A method of fastening one end of dental floss 2 according to the present invention may be best described with particular reference to FIG. 5. The method includes first inserting one end of dental floss 2 into slot 22 toward substantially the bottom of slot 22 to retain dental floss 2 on retaining member 21 so that section 2a is on one side of retaining member 21 and section 2b is on the other side of retaining member 21 (A of FIG. 5). Accordingly, dental floss 2 extends from section 2a on one side of retaining member 21 into slot 22, runs along substantially the bottom of slot 22 between the substantially parallel lines of slot 22 to the other side of slot 22, and extends out from slot 22 to section 2b on the other side of retaining member 21. In the illustrated form of the invention, slot 22 is preferably integrally formed in retaining member 21 substantially on the opposite end of bottom 25 so that when dental floss 2 is retained in retaining member 21 with section 2a on one side of retaining member 21 and section 2b on the other side of retaining member 21, dental floss 2 must also be retained in slot 22 with sections 2a and 2b on either side of slot 22.

With dental floss 2 retained in slot 22 having section 2a on one side of retaining member 21 and section 2b on the other, the method continues with the step of winding section 2b substantially transversely around the external peripheral surface of retaining member 21 to substantially the opposite side of retaining member 21 so that section 2b is turned substantially transversely from one side to the other side (B of FIG. 5). Accordingly, section 2b is winding transversely around the external peripheral surface of retaining member 21 substantially one-half the external peripheral transverse length of retaining member 21 to be at the same side of section 2a. In the preferred illustrated form of the invention slot 22 cuts into retaining member 21 and divides retaining member 21 into two substantially semicircular pieces of material. Accordingly, it takes substantially one-half the external peripheral transverse length of retaining member 21 for section 2b to reach or extend from one side of retaining member 21 to the other side.

Having sections 2a and 2b on the same side of retaining member 21, the preferred method of fastening one end of dental floss 2 continues with the step of inserting section 2b into slot 22 from the same side of section 2a to the opposite side of section 2a toward substantially the bottom of slot 22; therefore, section 2b is pulled by a downward force to substantially the bottom of slot 22 and, at the same time, an outward force is applied to pull section 2b to the opposite side of section 2a so that section 2b extends out from substantially the bottom of slot 22 to the opposite side of section 2a. As a result, dental floss 2 is securely fastened in slot 22 and retaining member 21 (C of FIG. 5). The downward and outward pull of section 2b to insert dental floss 2 toward substantially the bottom of slot 22 will not only pull section 2b toward the bottom of slot 22 but also tighten the winding portion of dental floss 2 tightly against retaining member 21 so that dental floss 2 is securely fastened in slot 22 and retaining member 21. In the illustrated form of the invention slot 22 comprises preferably two substantially parallel lines having a perpendicular distance substantially equal to zero so that dental floss 2 is tightly compressed or flattened between slot 22. Accordingly, the downward and outward pull of section 2b securely fastens dental floss 2 in slot 22 and retaining member 21.

The preferred method of fastening one end of dental floss 2 in the step of inserting into slot 22 also includes the step of inserting dental floss 2 into notch 26 before inserting dental floss 2 into slot 22. When dental floss 2 is in notch 26, the only action required to insert dental floss 2 into slot 22 is a downward force applied to dental floss 2 to insert dental floss 2 toward the bottom of slot 22. In the preferred form of the invention slot 22 connects with notch 26 at connection line 28 which is remote from the opening cut of notch 26. As a result, dental floss 2 is received by notch 26 before dental floss 2 is inserted into slot 22.

FIG. 6 illustrates a dental floss holder 84 which is substantially identical to dental floss holder 82 (FIG. 5), except that the perpendicular distance between the two substantially parallel lines of a slot 42 is substantially equal to or slightly larger than the cross-sectional dimension of dental floss 2. A similar method of fastening one end of dental floss 2 on dental floss holder 84 is illustrated in FIG. 6. The similar method is substantially identical to the method described in FIG. 5, except that the step of winding (B of FIG. 6) includes winding section 2b several times transversely around the external peripheral surface of a retaining member 41 to clamp section 2a tightly against retaining member 41. As a result, section 2a is tightly clamped against retaining member 41 by the winding portion of dental floss 2. The similar method continues with inserting section 2b into slot 42 (C of FIG. 6). Section 2b is inserted into slot 42 (section 2b may be inserted into slot 42 from any one of the two sides of slot 42) and section 2b is also pulled by a downward and outward force such that the winding portion of dental floss 2 is securely tightened against retaining member 41 so that section 2a is securely clamped by the tightened winding portion of dental floss 2 against retaining member 41. Similarly, the downward and outward force applied to section 2b to insert dental floss 2 toward substantially the bottom of slot 42 will not only pull section 2b toward the bottom of slot 42 but also tighten the winding portion of dental floss 2 tightly against retaining member 41 with section 2a tightly clamped between retaining member 41 and the winding portion. As a result, dental floss 2 is tightly fastened. Similar reference numerals are used in FIGS. 5 and 6, except that in FIG. 6, the reference numbers are in the forties. Otherwise, the same result of fastening one end of dental floss 2 is achieved by substantially the same method of using dental floss holders 82 and 84 in FIGS. 5 and 6.

Winding section 2b around retaining member 21 is preferred in the illustrated form of the invention; however, it is understood that winding section 2a around retaining member 21 will achieve the same resultant effects. It is also understood that winding several times around retaining member 21 will further enhance the fastening function. Therefore, it is understood that repeating the steps of B and C in FIG. 5 several times will extremely tightly fasten dental floss 2 on dental floss holder 82; however, repeating the steps of B and C in FIG. 5 will also work for dental floss holder 84. By the same token, applying the winding method described in FIG. 6 for dental floss holder 84 to dental floss holder 82 will, of course, extremely tightly fasten dental floss 2.

FIG. 7 illustrates an embodiment similar to that of FIG. 2, except that a notch 66 is formed on the side of a retaining member 61. Similar reference numerals are used in FIGS. 7 and 2, except that the reference numbers in FIG. 7 are in the sixties. Otherwise, the embodiment of FIG. 7 is substantially identical to that of FIG. 2 in operation, in resultant effects and substantially in structure.

Although the description above contains many specifications, these should not be construed as limiting the scope of the invention but as merely providing illustrations of some of the presently preferred embodiments of this invention. Thus the scope of the invention should be determined by the appended claims and their legal equivalents, rather than by the examples given.

We claim:

1. A dental floss holder for fastening one end of a dental floss, said holder comprising:

a retaining member adapted to be handled by fingers, whereby the floss may be held against said retaining member to facilitate the retention of the floss; and said retaining member having a slot thereacross substantially at one end thereof and extending toward generally the opposite end thereof to an intermediate position, said slot comprising two substantially parallel configurations having a substantially perpendicular distance therebetween selected from substantially equal to the cross section of the floss to substantially equal to zero, whereby the floss may be fastened in said holder by inserting the floss into said slot such that the floss has two sections each extending out from each side of said slot, winding one of the sections around said retaining member from one side of said slot to the opposite side at least once, and then inserting said one of the sections into said slot to fasten the floss therein, whereby when the floss is fastened in said slot of said holder, said holder having the floss fastened therein is manipulated by a hand in lieu of winding the floss around a finger for teeth cleaning.

2. The holder of claim 1, further comprising receiving means for receiving the floss into said slot, said receiving means comprising a notch defining an angular cut formed substantially at one end of said retaining member, said notch connecting to said slot at a connection line to facilitate the insertion of the floss into said slot.

3. The holder of claim 2, wherein said angular cut is selected from about 40° to about 120°.

4. The holder of claim 2, wherein said notch has a longitudinal length about one-tenth that of said retaining member.

5. The holder of claim 1, wherein said slot has a longitudinal length about one-half that of said retaining member.

6. The holder of claim 1, wherein said retaining member comprises a generally elongated configuration.

7. A dental floss holder for fastening one end of a length of dental floss, said holder comprising:

a retaining member; and fastening means for fastening the floss, said fastening means comprising a slot across substantially at one end of said retaining member and extending toward generally the opposite end of said retaining member to an intermediate position, said slot defining an opening having two substantially parallel configurations adjacent to each other closely so as to fasten the floss therebetween, whereby when the floss is fastened in said slot of said fastening means, the floss has two sections each extending out from each side of said slot, whereby when the floss is fastened in said fastening means of said holder, said holder having the floss fastened therein is manipulated by a hand in lieu of winding the floss around a finger for teeth cleaning.

8. The holder of claim 7, further comprising receiving means for receiving the floss into said slot, said receiving means comprising a notch defining an angular cut formed substantially at one end of said retaining member, said notch connecting to said slot at a connection line to facilitate the insertion of the floss into said slot.

9. The holder of claim 8, wherein said angular cut is selected from about 40° to about 120°.

10. The holder of claim 8, wherein said notch has a longitudinal length about one-tenth that of said retaining member.

11. The holder of claim 7, wherein said parallel configurations have a substantially perpendicular distance selected from substantially equal to the cross section of the floss to substantially equal to zero.

12. The holder of claim 7, wherein said slot has a longitudinal length about one-half that of said retaining member.

13. The holder of claim 7, wherein said retaining member comprises a generally elongated configuration adapted to be handled by fingers.

14. A dental floss holder for fastening one end of a dental floss, said holder comprising:

a retaining member adapted to be handled by fingers, whereby the floss may be held by fingers against said retaining member to facilitate the retention of the floss; and said retaining member having a slot thereacross substantially at one end thereof and extending toward generally the opposite end thereof to an intermediate position, whereby when the floss is fastened in said slot, the floss has two sections each extending out from each side of said slot, said slot comprising two substantially parallel configurations having a substantially perpendicular distance therebetween selected from substantially equal to the cross section of the floss to substantially equal to zero, whereby when the floss is fastened in said slot of said holder, said holder having the floss fastened therein is manipulated by a hand in lieu of winding the floss around a finger for teeth cleaning.

15. The holder of claim 14, further comprising receiving means for receiving the floss into said slot, said receiving means comprising a notch defining an angular cut formed substantially at one end of said retaining member, said notch connecting to said slot at a connection line to facilitate the insertion of the floss into said slot.

16. The holder of claim 15, wherein said angular cut is selected from about 40° to about 120°.

17. The holder of claim 15, wherein said notch has a longitudinal length about one-tenth that of said retaining member.

18. The holder of claim 14, wherein said slot has a longitudinal length about one-half that of said retaining member.

19. The holder of claim 14, wherein said retaining member comprises a generally elongated configuration.

20. A dental floss device for fastening a length of dental floss, said device comprising:

two separate dental floss holders, each of said holders for fastening each end of the floss, at least one of said holders comprising:

a retaining member adapted to be handled by fingers, whereby the floss may be held against said retaining member to facilitate the retention of the floss; and said retaining member having a slot thereacross substantially at one end thereof and extending toward generally the opposite end thereof to an intermediate position, said slot comprising two substantially parallel configurations having a substantially perpendicular distance therebetween selected from substantially equal to the cross section of the floss to substantially equal to zero, whereby when one end of the floss is fastened in said slot, the floss has two sections each extending out from each side of said slot, whereby when each end of the floss is fastened in each of said holders, each of said holders is manipulated by a hand in a spaced apart relationship for teeth cleaning.

21. The device of claim 20, wherein said at least one of said holders further comprises receiving means for receiving the floss into said slot, said receiving means comprising a notch defining an angular cut formed substantially at one end of said retaining member, said notch connecting to said slot at a connection line to facilitate the insertion of the floss into said slot.

22. The device of claim 21, wherein said angular cut is selected from about 40° to about 120°.

23. The device of claim 21, wherein said notch has a longitudinal length about one-tenth that of said retaining member.

24. The device of claim 20, wherein said slot of said at least one of said holders has a longitudinal length about one-half that of said retaining member.

25. The device of claim 20, wherein said retaining member of said at least one of said holders comprises a generally elongated configuration.

26. A method of fastening one end of a dental floss in a dental floss holder, which comprises the steps of:

inserting the floss into said holder such that the floss has two sections each extending out from each side of said holder;

winding one of the two sections around said holder from one side to the other side at least once; and inserting said one of the two sections into said holder to fasten the floss therein, whereby when the floss is fastened in said holder, said holder having the floss fastened therein is manipulated by a hand in lieu of winding the floss around a finger for teeth cleaning.

27. The method of claim 26, wherein each inserting step is performed by inserting the floss into a slot of said holder.

28. The method of claim 26, wherein each inserting step is performed by inserting the floss through a notch into a slot.

* * * * *